(12) United States Patent
Garcia Gutierrez et al.

(10) Patent No.: US 11,524,183 B1
(45) Date of Patent: Dec. 13, 2022

(54) SYSTEM, APPARATUS, AND METHOD FOR DELIVERING ULTRASOUND

(71) Applicant: SONABLATE CORP., Charlotte, NC (US)

(72) Inventors: Carlos Martin Garcia Gutierrez, Jalisco (MX); Narendra Sanghvi, Indianapolis, IN (US); Habid Becerra Herrejon, Jalisco (MX)

(73) Assignee: SONABLATE CORP., Charlotte, NC (US)

( * ) Notice: Subject to any disclaimer, the term of this patent is extended or adjusted under 35 U.S.C. 154(b) by 0 days.

(21) Appl. No.: 17/654,474

(22) Filed: Mar. 11, 2022

(51) Int. Cl.
*A61N 7/02* (2006.01)
*A61B 18/00* (2006.01)

(52) U.S. Cl.
CPC ...... *A61N 7/02* (2013.01); *A61B 2018/00577* (2013.01)

(58) Field of Classification Search
CPC .................. A61N 7/02; A61B 2018/00577
See application file for complete search history.

(56) References Cited

U.S. PATENT DOCUMENTS

| | | | |
|---|---|---|---|
| 5,895,356 | A | 4/1999 | Andrus et al. |
| 6,071,239 | A | 6/2000 | Cribbs et al. |
| 6,419,648 | B1 | 7/2002 | Vitek et al. |
| 8,727,987 | B2 | 5/2014 | Chauhan |
| 9,268,015 | B2 | 2/2016 | Rotheberg et al. |
| 9,770,605 | B2 | 9/2017 | Darlington et al. |
| 10,016,627 | B2 | 7/2018 | Vitala et al. |
| 10,182,792 | B2 | 1/2019 | Johnson et al. |
| 10,300,308 | B2 * | 5/2019 | Seip .......................... A61N 7/02 |
| 10,888,718 | B2 | 1/2021 | Barthe et al. |
| 2005/0038340 | A1 * | 2/2005 | Vaezy ...................... A61B 8/06 |
| | | | 600/458 |
| 2008/0183077 | A1 | 7/2008 | Moreau-Gobard et al. |

(Continued)

OTHER PUBLICATIONS

Sanghvi et al., "Noninvasive surgery of prostate tissue by high intensity focused ultrasound: an updated report", 1999, European Journal of Ultrasound, pp. 19-29 (Year: 1999).*

(Continued)

*Primary Examiner* — Pascal M Bui Pho
*Assistant Examiner* — Adil Partap S Virk
(74) *Attorney, Agent, or Firm* — Mark T. Vogelbacker; Eckert Seamans Cherin & Mellott, LLC

(57) ABSTRACT

A method can include placing a high intensity focused ultrasound (HIFU) probe proximate a first location of a designated treatment volume of a patient. The probe can include at least one transducer. The method can also include energizing the transducer to ablate a first lesion on or in the designated treatment volume, de-energizing the transducer, and focusing or moving the transducer to a second location on or in the designated treatment volume. The method can also include reenergizing the transducer to ablate a second lesion on or in the treatment volume, de-energizing the transducer, and focusing or moving the transducer to a third location on or in the designated treatment volume. The method can further include reenergizing the transducer to ablate a third lesion on or in the treatment volume, and de-energizing the transducer.

12 Claims, 6 Drawing Sheets
(2 of 6 Drawing Sheet(s) Filed in Color)

(56) References Cited

U.S. PATENT DOCUMENTS

| | | | |
|---|---|---|---|
| 2008/0275445 A1* | 11/2008 | Kelly | A61B 18/18 606/45 |
| 2009/0012512 A1* | 1/2009 | Utley | A61B 18/1492 606/34 |
| 2009/0088623 A1* | 4/2009 | Vortman | A61B 8/5276 601/3 |
| 2011/0306880 A1* | 12/2011 | Li | A61B 8/08 600/443 |
| 2012/0016239 A1* | 1/2012 | Barthe | A61B 8/4272 600/439 |
| 2012/0029353 A1* | 2/2012 | Slayton | A61B 18/1492 606/34 |
| 2012/0150035 A1 | 6/2012 | Seip et al. | |
| 2013/0116548 A1* | 5/2013 | Kumar | A61B 8/463 600/424 |
| 2017/0000376 A1* | 1/2017 | Partanen | A61B 18/18 606/45 |
| 2017/0239498 A1 | 8/2017 | Hill | |
| 2017/0319875 A1 | 11/2017 | Carol et al. | |
| 2020/0023207 A1 | 1/2020 | Carol | |

OTHER PUBLICATIONS

Enholm et al., "Improved Volumetric MR-HIFU Ablation by Robust Binary Feedback Control", Jan. 4, 2010, IEEE Transactions on Biomedical Engineering, vol. 57 No. 1, pp. 103-113 (Year: 2010).*

Ellens et al, "The utility of sparse 2D fully electronically steerable focused ultrasound phased arrays for thermal surgery: a simulation study", 2011, Institute of Physics and Engineering in Medicine, pp. 4913-4932 (Year: 2011).*

Barnat et al., "Noninvasive vascular occlusion with HIFU for venous insufficiency treatment: preclinical feasibility experience in rabbits", Jan. 7, 2019, Physics in Medicine and Biology, pp. 1-9 (Year: 2019).*

Fura et al., "Experimental evaluation of targeting accuracy of ultrasound imaging-guided robotic HIFU ablative system for the treatment of solid tumors in pre-clinical studies", 2021, Applied Acoustics, pp. 1-9 (Year: 2021).*

* cited by examiner

SYSTEM, APPARATUS, AND METHOD FOR DELIVERING ULTRASOUND

FIELD

The presently disclosed technology relates generally to efficiently and effectively delivering ultrasound. More specifically, in one embodiment, the presently disclosed technology is directed to applying High Intensity Focused Ultrasound (HIFU) in a checkerboard pattern, such that a lesion is created at every other adjacent spot in a designated treatment volume of a patient, to treat, for example, prostate cancer (PCa) and/or Benign Prostatic Hyperplasia (BPH).

BACKGROUND AND DESCRIPTION OF RELATED ART

Use of focused ultrasound (aka, HIFU) is a beneficial way to treat certain medical conditions or ailments. Over the last two decades, focused ultrasound treatments have evolved, from initially treating the entire prostatic gland to treating only a focal lesion (also known as an index lesion). This allowed for managing early and intermediate (localized) stage (T1/T2) prostate cancer (Gleason score<7) via a Focal PCa treatment with an ultrasound device. Delivering HIFU with ultrasound guidance to the entire prostate volume @40cc takes approximately 4 hours.

HIFU devices, such as HIFU probes, use focused ultrasound to deliver a thermal and/or cavitation dose of energy to a small, well-defined tissue volume at some fixed or focal distance from a surface of a transducer of the device. This technique and family of devices are described in more detail in U.S. Pat. Nos. 10,300,308 and 10,182,792, and U.S. Application Publication Nos. 2020/0023207 and 2017/0319875, which are hereby incorporated by reference.

The transducer is connected to two motors inside the probe, which can be automated or computer-controlled. The motions of the motors are orthogonal in space. These motors can be used to scan the ultrasound transducer in two orthogonal planes to image and ablate the prescribed or designated tissue volume specified in a treatment plan on the ultrasound images.

In the prior art, the scanning process in each plane is performed with a fixed distance between treatment sites, with prescribed ultrasound energy. This provides or creates an overlapping or at least contacting of individual thermal lesions to produce a large contiguous volume lesion of a several cubic centimeters in size.

For example, FIG. 1 shows FIG. 1C of U.S. Pat. No. 10,300,308, where a designated treatment volume 14 (e.g., tissue) within a patient is targeted by a transducer 18 of an ultrasound probe through an ultrasound beam 16. Individual lesions 10 are created in overlapping or abutting contact within the designated treatment volume 14, thereby creating a continuous treatment region. The lesions 10 are created in accordance with a treatment plan 12.

SUMMARY

Despite the numerous benefits of the prior art, there is a need for an improved system that more quickly, easily, and efficiently deliver ultrasound to a patient. For example, the creation of continuous treatment sites results in volumetric heating of the treated tissue, which can cause subsequent edema, inflammation of tissue (e.g., the prostate gland), and can prolong the need for urinary diversion through a Foley catheter. The inclusion of the urethra in the ablation prolongs the catheterization time by up to 3 weeks. Further, injury caused by means of thermal ablation technique where the targeted tissue temperature is elevated less than boiling results in a coagulative tissue necrosis can result in a prolonged total elimination of the necrotic tissue by up to 2 months. In addition, treated tissue, in the form of sloughed tissue, which in the case of a predominance of fibrous tissue in the adenoma, can form obstructive, continuous accumulations that even require removal by means of TURP to achieve spontaneous urination.

The presently disclosed technology overcomes the above and other drawbacks of the prior art.

In particular, the treatment or planning technique of the present technology allows, by means of alternate treatment sites, to reduce the treatment time by approximately one third. Further, the presently disclosed technology allows for less excessive heating of the treated tissue, since the intended phenomenon is boiling or cavitation (therefore, gaseous transformation of semisolid tissue hence spontaneous mechanical disintegration of cellular matrix) of the adenoma. This phenomenon considerably reduces periurethral edema and prostate gland inflammation. Together with the preservation of the urethra in a minimum of 80% of its length, both phenomena result in a catheterization time of 4 to 7 days. Due to the cavitation or boiling of the treated tissue, the elimination of such is basically achieved by reabsorption. With this technique, Applicants have yet to observe obstruction due to the presence of residual accumulations, such as those described above.

In one optional embodiment, the presently disclosed technology is directed to a method that can include placing a high intensity focused ultrasound (HIFU) probe proximate a first location of a designated treatment volume of a patient. The probe can include at least one transducer. The method can also include energizing the transducer to ablate a first lesion on or in the designated treatment volume, de-energizing the transducer, and focusing or moving the transducer to a second location on or in the designated treatment volume. The method can also include reenergizing the transducer to ablate a second lesion on or in the treatment volume, de-energizing the transducer, and focusing or moving the transducer to a third location on or in the designated treatment volume. The method can further include reenergizing the transducer to ablate a third lesion on or in the treatment volume, and de-energizing the transducer.

In another optional embodiment, the presently disclosed technology is directed to a method that can include receiving a two-dimensional or three-dimensional rendering of a designated treatment volume of a patient. The designated treatment volume can be a macroscopic three-dimensional volume located beneath subcutaneous fat of the patient. The method can include planning HIFU ablation treatment plan that includes identification of individual treatment sites on any of three planes of the three-dimensional rendering. The method can include placing a HIFU probe proximate a first location of the designated treatment volume of the patient. The probe can include at least one transducer. The method can include energizing the transducer to deliver a thermal or cavitation dose of energy to ablate a first lesion on or in the designated treatment volume, then de-energizing the transducer, and then focusing or moving the transducer to a second location on or in the designated treatment volume. The first location can be spaced-apart from the second location. The method can further include reenergizing the transducer to deliver a thermal or cavitation dose of energy to ablate a second lesion on or in the treatment volume, then de-energizing the transducer, and then focusing or moving the transducer to a third location on or in the designated treatment volume. The third location can be spaced-apart from each of the first and second locations. The method can further include reenergizing the transducer to deliver a thermal or cavitation dose of energy to ablate a third lesion on or in the treatment volume, and then de-energizing the transducer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the presently disclosed technology, will be better understood when read in conjunction with the appended drawings, wherein like numerals designate like elements throughout. For the purpose of illustrating the presently disclosed technology, there are shown in the drawings various illustrative embodiments. It should be understood, however, that the presently disclosed technology is not limited to the precise arrangements and instrumentalities shown. In the drawings.

DETAILED DESCRIPTION

Figure 1:
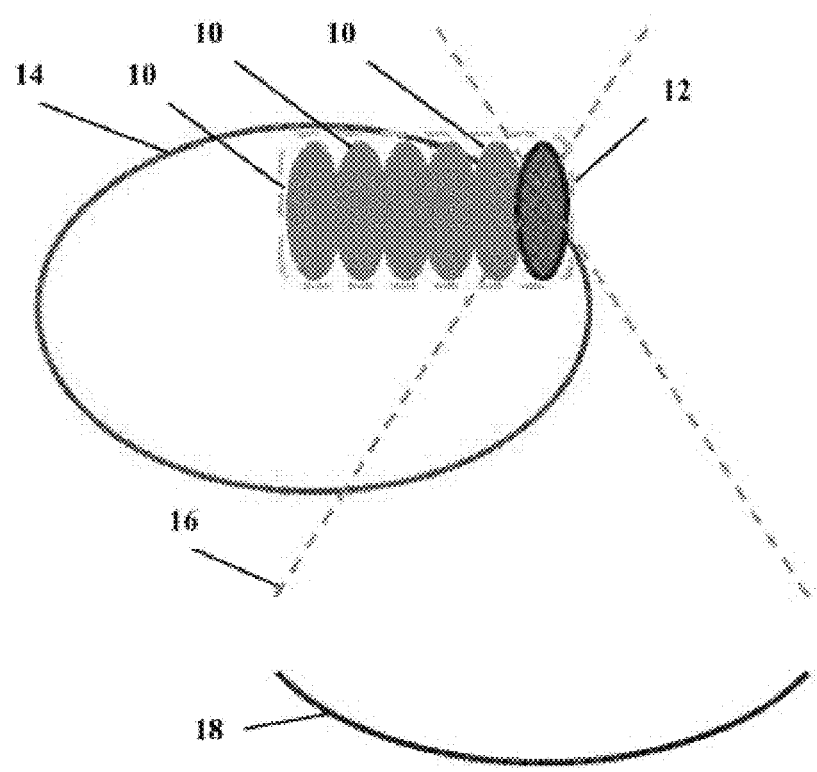
FIG. 1 is a schematic view of the creation of a multitude of focal lesions after successive HIFU "ON" and "OFF" cycles in accordance with the prior art.

While systems, devices and methods are described herein by way of examples and embodiments, those skilled in the art recognize that the presently disclosed technology is not limited to the embodiments or drawings described. Rather, the presently disclosed technology covers all modifications, equivalents and alternatives falling within the spirit and scope of the appended claims. Features of any one embodiment disclosed herein can be omitted or incorporated into another embodiment.

Any headings used herein are for organizational purposes only and are not meant to limit the scope of the description or the claims. As used herein, the word "may" is used in a permissive sense (i.e., meaning having the potential to) rather than the mandatory sense (i.e., meaning must). Unless specifically set forth herein, the terms "a," "an" and "the" are not limited to one element but instead should be read as meaning "at least one." The terminology includes the words noted above, derivatives thereof and words of similar import.

Referring now in detail to the figures, wherein like reference numerals refer to like parts throughout, FIGS. 2-6 show a system, apparatus and method of using or delivering ultrasound through a checkerboard or spacing pattern that does not target or address each and every point in a designated treatment volume. This checkerboard pattern is independent of tissue characteristics. In one particular embodiment, the presently disclosed technology optionally includes delivering HIFU for the treatment of benign prostatic hyperplasia (BPH), for example, and due to the checkerboard or spacing pattern can be performed or completed in approximately 30 to 45 minutes, as the prostate is only partially ablated near the bladder neck and around urethra.

The reduced treatment time of the presently disclosed technology, as compared to the prior art, manifests itself in reduced catheterization time post-treatment, less or no damage to the urethra, no incontinence, and/or no effect on erectile function. Thus, an important purpose of the presently disclosed technology is to reduce the overall treatment time, resulting in reduced post HIFU catheterization time and morbidity, while maintaining a good urinary flow outcome and reductions of symptoms, and while improving the quality-of-life index.

Figure 2:
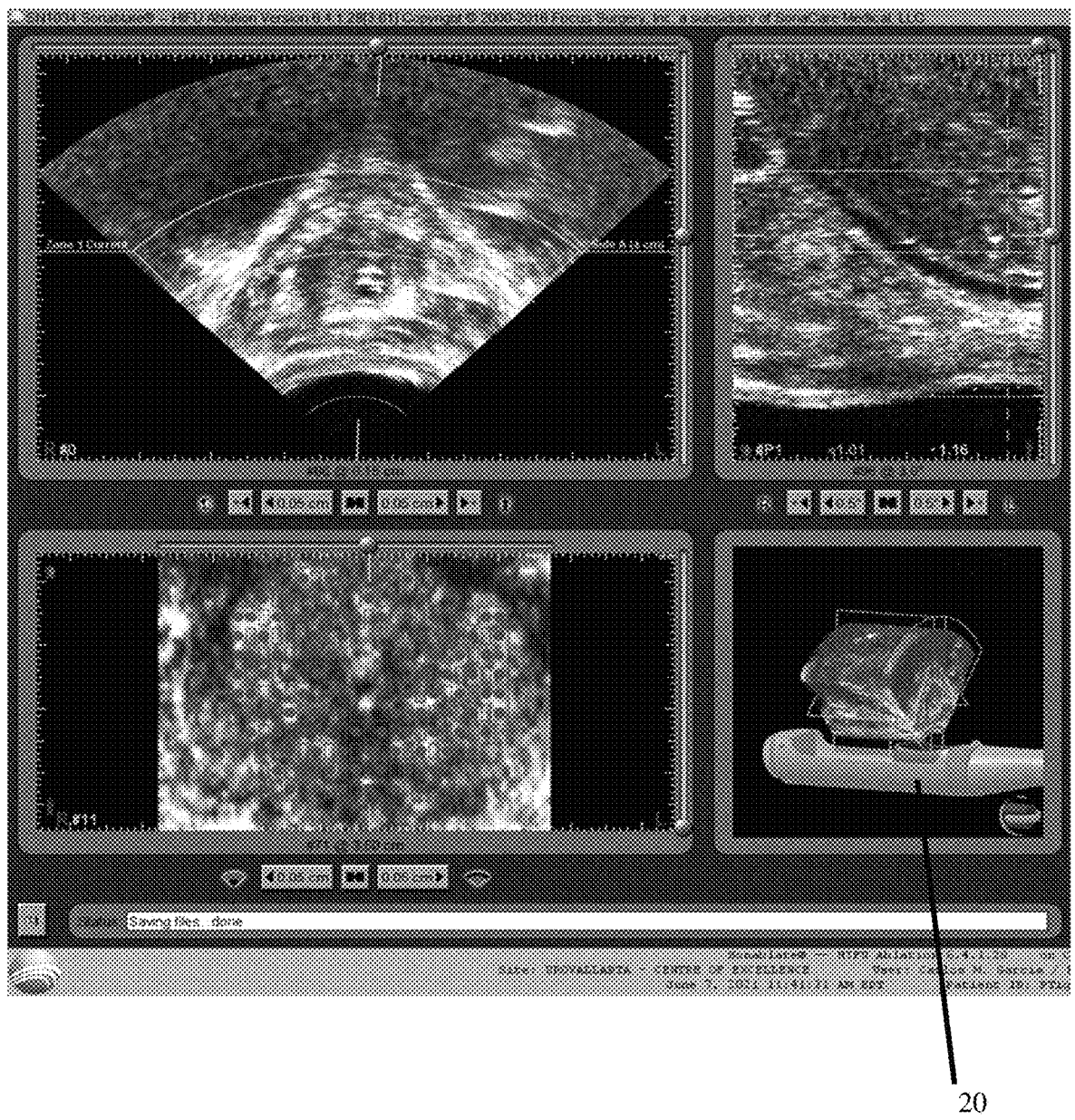
FIG. 2 shows various computer representations of a designated treatment volume according to an embodiment of the presently disclosed technology.
Figure 5:
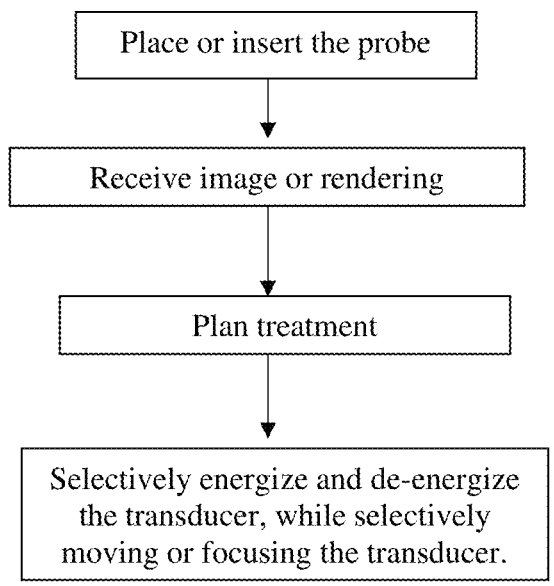
FIG. 5 is a flow diagram of one embodiment of the presently disclosed technology.

In particular, in one embodiment, as shown in FIGS. 2 and 5, the presently disclosed technology can include receiving a two-dimensional or three-dimensional image or computer rendering of a designated treatment volume, such as but not limited to a prostate, of a patient. The image or rendering can optionally include a grid. The designated treatment volume can be a macroscopic three-dimensional volume located beneath subcutaneous fat of the patient. Despite the above reference to the prostate, the presently disclosed technology can be beneficial for a variety of different organs or glands. In fact, the presently disclosed technology can be utilized for any tissue (e.g., breast or uterine fibroid, fat, etc.), though the efficacy may differ depending upon the tissue treated.

Optionally, the image or rendering received or created can have two or more components or sub-images. For example, the imaging allows the user to view slices of tissue of an organ or gland, such as a prostate, in sagittal, transverse, and/or coronal planes, as shown in the upper left, upper right, and lower left corners of FIG. 2, respectively. A fourth sub-image, such as that shown in the lower right corner of FIG. 2, can be a perspective view of a portion of a probe proximate a designated treatment volume. In one embodiment, all locations and contents of the image planes or any other sub-images can be stored in computer memory by the software. As a result, a click of a cursor in any location on one of these planes can simultaneously display the other two image planes.

Figure 3:
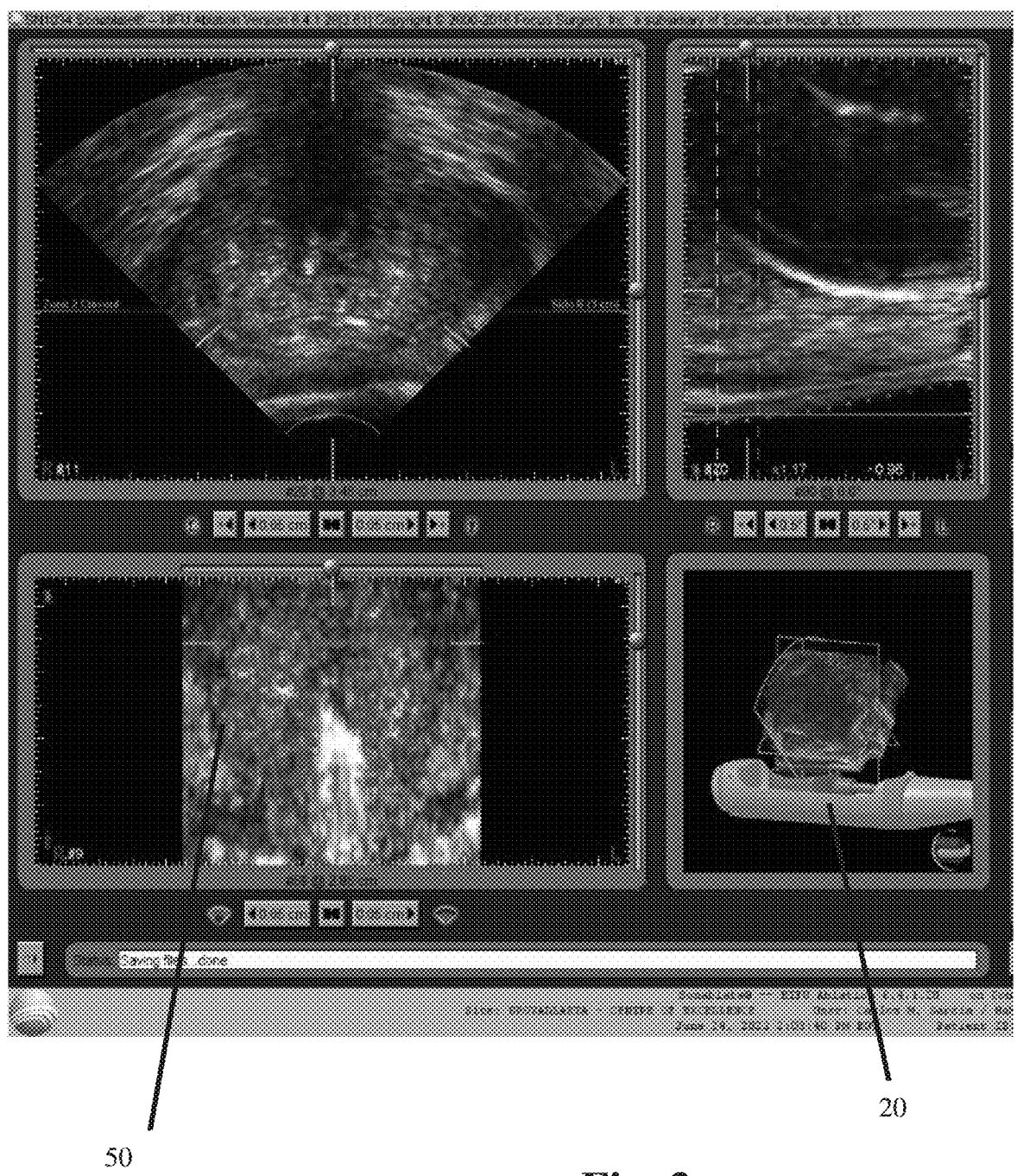
FIG. 3 shows various computer representations of a treatment plan according to an embodiment of the presently disclosed technology.

In one embodiment, as shown in FIGS. 3 and 5, the presently disclosed technology can include planning a high intensity focused ultrasound (HIFU) ablation treatment that can include identifying individual treatment sites on any or each of three planes of the three-dimensional rendering. Optionally, using the treatment planning software with volume visualization, the user can plan a HIFU ablation treatment, which can consist of the placement of individual treatment sites (one of several of which is shown by a circular or oval dot 50 in FIG. 3) on any or each of the three planes. Together, these treatment sites 50 form the targeted treatment volume plan.

Optionally, the presently disclosed technology can include addressing, treating, and/or ablating each treatment site 50 individually and/or in series. This can include creating a plurality of spaced-apart and non-contacting or non-overlapping lesions, one of which can correspond to one of the treatment sites 50. In one embodiment, one of the plurality of spaced-apart lesions is created at every other adjacent spot or node on the grid to create the checkerboard pattern. The point(s), area(s), or volume(s) between the lesions can, at least initially, be non-ablated tissue.

In one optional embodiment, the spacing of treatment sites 50 is fixed at or approximately 3 mm between adjacent sites, or at or approximately 6 mm when every other site is skipped, as would be required for the checkerboard pattern. However, other spacings are possible. In general, the size/spacing is determined by the characteristics of the size of the thermal lesion the focal zone of the transducer creates. In one optional embodiment, the (adjacent) spacing should not be larger than the width of the focal zone, as otherwise, untreated tissue is left in between the sites. However, with the checkerboard pattern, a 2x focal zone width is used for the spacing, but with increased power to compensate for the places in the treatment plan where no lesion is created. Optionally, 2x spacing of the treatment sites 50 can be created, where "x" is a variable that equals the focal zone dimensions of the HIFU beam.

In general, the shape of each treatment site 50 is determined by the characteristics of the HIFU transducer. Usually, HIFU transducers are circular or slightly oval in shape in the plane shown in FIG. 3 (showing the cross-section of a treatment site 50). In three-dimensions, the treatment sites 50 can have the shape of a rice-kernel, for example oval in one cross-section, circular in the other.

The following example describes the creation of three separate lesions in series. However, the presently disclosed technology can include the creation of four or more, such as fifty or more, lesions. The total number of lesions created can depend upon several different factors, including the type of ailment being treated and/or the aggressiveness of the ailment.

For example, in one embodiment, the presently disclosed technology can include placing a HIFU probe 20 proximate a first location of the designated treatment volume of the patient. The probe 20 can include at least one transducer 18. The transducer 18 can be energized (e.g., adjusted to an ON state in the duty cycle) to deliver a thermal or cavitation dose of energy to ablate a first lesion on or in the designated treatment volume. Optionally, the first lesion and any other individual lesion discussed herein can have a predetermined volume, such as but not limited to the dimensions of or approximately 3×3×10 mm$^3$ or of or approximately 3×3×12 mm$^3$. In other embodiments, individual leans could range from 1×1×5 mm$^3$ to 5×5×15 mm$^3$.

There are trade-offs related to the size of the lesions created. For example, larger lesions cover a desired treatment plan or volume faster. However, larger lesions cannot confirm as easily to the treatment plan, as inevitably parts of the larger treatment sites will be outside of a desired treatment plan. FIG. 2, for example, shows that the prostate boundary is curved, and if treatment sites are placed there, in some cases the entire treatment site will be inside the gland, which is desirable. However, in other cases a part of the treatment site will be inside the gland, and the other part outside of the gland, which is not desirable. Smaller treatment sites conform better to the boundaries of a treatment plan (e.g., smaller treatment sites "won't stick out as much"), but will ablate only a smaller tissue volume each time, thus likely increasing treatment time. The tradeoff is between speed and precision.

Each ultrasound dose can be controlled using short ultrasound bursts of few to several thousand milliseconds, while controlling the ultrasound pressure amplitude to produce boiling bubbles at selected lesion or checkerboard sites. Boiling tissue by means of cavitation is known as "Boiling Histotripsy" and can be used to efficiently ablate/kill and remove BPH tissue from the gland. Boiling of tissue will gasify the tissue thus unostentatiously removing the treated tissue and making a large cavity in the prostate gland. The efficient removal of tissue reduces catheter time and improves urine flow with the reduction of BPH symptoms.

Following creation or completion of the first lesion, the transducer 18 can then be de-energized. For example, the transducer 18 can be adjusted to an OFF state in the duty cycle. The range of time in the OFF state can be anywhere from a few milliseconds to several seconds. For a thermal effect, it can be necessary to wait for the heat to dissipate, e.g., for 3-12 seconds, given typical blood flows and cooling apparatus. The exact amount of time can be determined by the healthcare professional and/or the treatment plan to strike the right balance between treatment time minimization (which needs short ON times and short OFF times), efficacy (which need longer ON times but shorter OFF times), and treatment safety (which need short ON times but longer OFF times), as dialed-in and verified with clinical studies.

Next, the transducer 18 can be focused on or moved to or toward a second location on or in the designated treatment volume. The first location is spaced-apart from the second location, optionally by exactly or approximately the width of one lesion. Other spacings are also possible, but are tissue independent, and apply to both dimensions of the treatment plan. Thus, the spacing is not arbitrary, but instead is predetermined as part of the treatment plan. The transducer 18 can be reenergized (e.g., adjusted to an ON state in the duty cycle) to deliver a thermal or cavitation dose of energy to ablate a second lesion on or in the treatment volume.

The transducer 18 can then be de-energized. For example, the transducer 18 can be adjusted to an OFF state in the duty cycle. Next, the transducer 18 can be focused on or moved to or toward a third location on or in the designated treatment volume. The third location can be spaced-apart from each of the first and second locations, at the same spacing as described above. The transducer 18 can be reenergized (e.g., adjusted to an ON state in the duty cycle) to deliver a thermal or cavitation dose of energy to ablate a third lesion on or in the treatment volume. The transducer can then be de-energized. Optionally, none of the first lesion, the second lesion, the third lesion, or any other lesion created by the method contact or overlap.

Optionally, once the treatment plan is defined, the software can follow the plan sequentially and places or creates at each treatment site a HIFU-induced individual lesion, which together will coalesce into the desired volumetric lesion needed for the treatment of the ailment, such as BPH or PCa. Typically, the desired volumetric lesion coalesces by the end of the treatment plan. In one embodiment, the first line of treatment is located on a plane at a fixed distance from the transducer, the first plane is usually given by the 4 cm (focal point) transducer. Then each 3×3×10 mm$^3$ lesion is placed starting from the bladder neck, including the whole adenoma. The urethra is then localized using the Foley catheter as a guide and spared from the treatment.

In one embodiment, delivering the focused ultrasound energy in accordance with the targeted treatment plan includes the transducer being moved into or focused on the exact location of each treatment site to deliver the desired HIFU dose by the probe motors and amplifier. This process is repeated until all treatment sites of the plan have been visited by the HIFU transducer, and an individual HIFU lesion has been created at each treatment site. A flow diagram of one embodiment of this treatment is shown in FIG. 5.

In one embodiment, the HIFU transducer is energized for exactly or approximately 3 seconds ("HIFU ON time") to create each lesion. This process is followed by a "HIFU OFF time" or de-energizing of the transducer (e.g., exactly or approximately six seconds), which allows intervening tissue to cool to help manage the undesired build-up of thermal dose outside of the focal zone of the HIFU transducer. Incorrect management of the HIFU dose, incorrect interpretation of the ultrasound images acquired during the delivery of HIFU for treatment monitoring purposes, or incorrect pausing of the treatment when excessive heat build-up outside of the focal zone is ignored will lead to undesired adverse events and increased treatment morbidity.

With the proposed "checkerboard" treatment planning method, each treatment site (and hence each resulting lesion) is placed at every other adjacent spot, making sure that the discontinuous pattern is respected or maintained in both sagittal and transversal planes, as shown in FIG. 3.

Figure 4:
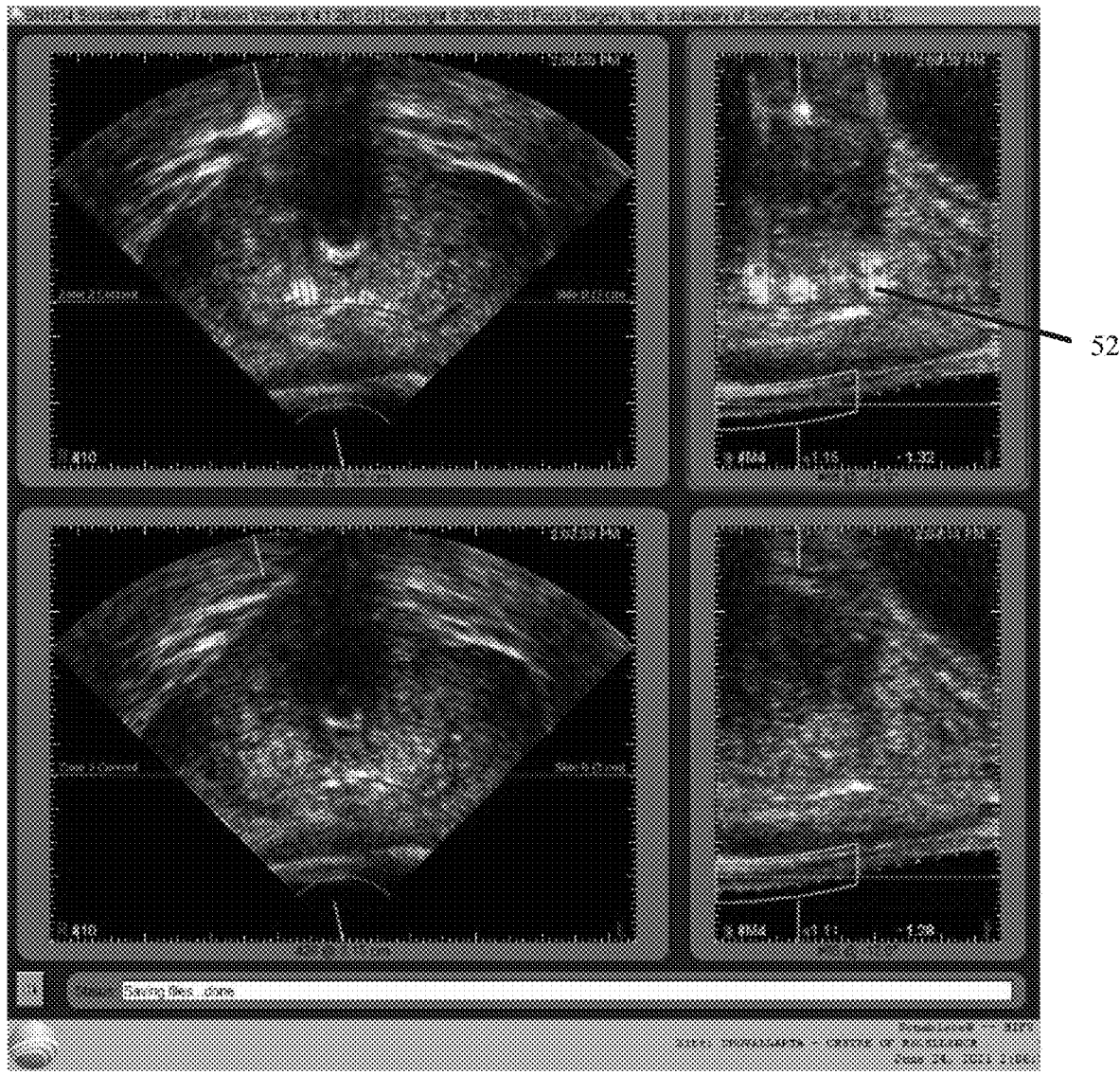
FIG. 4 shows various computer representations of the designated treatment volume following execution of the treatment plan according to an embodiment of the presently disclosed technology.

The ultrasound energy applied and/or adjusted to each treatment site is set to produce a tissue boiling or cavitation lesion, which is evidenced by a large and brighter echogenic change in the sagittal image, one of which is identified as reference 52 in FIG. 4. FIG. 4 depicts tissue boiling or cavitation visible as hyperechoic changes in post-HIFU delivery ultrasound images.

In one embodiment, once the device has delivered the energy to all the planned treatment sites, the system will allow the operator to continue with the next treatment section, which would then be defined by a new or second treatment plan. The new or second treatment plan could focus on another plane fixed at 4 cm or change the transducer with a focal point at 3 cm, depending on the adenoma's height or desired treatment target location.

Optionally, the transducer of the present disclosure can deliver ultrasound energy in a randomized fashion to reduce overlapping of beams that would result in reduced near field heating and more efficient energy delivery to focused locations.

A benefit of checkerboard pattern treatment plan is the need for fewer treatment sites than a regular or prior art treatment plan (such as that discussed in U.S. Pat. No. 10,300,308), which results in a reduced treatment time while still targeting and ablating the same overall tissue volume. As compared to the prior art or conventional HIFU power levels, HIFU delivery power in the presently disclosed technology needs to be increased, e.g., by 10-33%, 10-20%, or 20-33% higher based on tissue depth, to compensate for the point(s), area(s), or volume(s) of the designated treatment volume that are skipped in the checkerboard treatment plan to still generate a single or contiguous volumetric lesion and therapeutically effective treatment to the point of striving to achieve tissue boiling or cavitation. This achieved balance (while using fewer treatment sites but higher HIFU dose) overall results in a shorter treatment time with similar efficacy as a conventional treatment plan but with similar or lower morbidity.

Optionally, the power levels used for the present disclosure can be 26.4-31.92 W, or 42.7-492.1 W, depending for example on the type or side of transducer used. If the checkerboard treatment plan is applied with conventional HIFU power (e.g., when using a 4 cm focal length transducer, a typical power level is 37W, and when using a 3 cm focal length transducer, a typical power is 24W), untreated intervening tissue will be left behind in between the treatment sites. If the boiling or cavitation HIFU power is applied using a conventional treatment plan, excessive pre-focal heating will likely result, which can lead to adverse events and/or potential rectal wall damage. In one embodiment, both the checkerboard pattern and the increased HIFU boiling or cavitation energy levels need to be applied simultaneously to correctly implement the idea highlighted in this disclosure.

Optionally, characteristics of the tissue do not influence the checkerboard treatment plan of the presently disclosed technology. Thus, the checkerboard treatment plan of the presently disclosed technology is not tailored because of the presence of fat layers or characteristics of the tissue. In fact, the checkerboard treatment plan is completely independent of the tissue. The checkerboard treatment plan of the presently disclosed technology is implemented to save (e.g., reduce) treatment time while maintaining similar therapeutic performance One or more of the above-described techniques and/or embodiments can be implemented with or involve software, for example modules executed on one or more computing devices 210 (see FIG. 6). Of course, modules described herein illustrate various functionalities and do not limit the structure or functionality of any embodiments. Rather, the functionality of various modules may be divided differently and performed by more or fewer modules according to various design considerations.

Each computing device 210 may include one or more processing devices 211 designed to process instructions, for example computer readable instructions (i.e., code), stored in a non-transient manner on one or more storage devices 213. By processing instructions, the processing device(s) 211 may perform one or more of the steps and/or functions disclosed herein. Each processing device may be real or virtual. In a multi-processing system, multiple processing units may execute computer-executable instructions to increase processing power.

The storage device(s) 213 may be any type of non-transitory storage device (e.g., an optical storage device, a magnetic storage device, a solid-state storage device, etc.). The storage device(s) 213 may be removable or non-removable, and may include magnetic disks, magneto-optical disks, magnetic tapes or cassettes, CD-ROMs, CD-RWs, DVDs, BDs, SSDs, or any other medium, which can be used to store information. Alternatively, instructions may be stored in one or more remote storage devices, for example storage devices accessed over a network or the internet.

Each computing device 210 additionally may have memory 212, one or more input controllers 216, one or more output controllers 215, and/or one or more communication connections 1240. The memory 212 may be volatile memory (e.g., registers, cache, RAM, etc.), non-volatile memory (e.g., ROM, EEPROM, flash memory, etc.), or some combination thereof. In at least one embodiment, the memory 212 may store software implementing described techniques.

An interconnection mechanism 214, such as a bus, controller or network, may operatively couple components of the computing device 210, including the processor(s) 211, the memory 212, the storage device(s) 213, the input controller(s) 216, the output controller(s) 215, the communication connection(s) 1240, and any other devices (e.g., network controllers, sound controllers, etc.). The output controller(s) 215 may be operatively coupled (e.g., via a wired or wireless connection) to one or more output devices 220 (e.g., a monitor, a television, a mobile device screen, a touch-display, a printer, a speaker, etc.) in such a fashion that the output controller(s) 215 can transform the display on the output device 220 (e.g., in response to modules executed). The input controller(s) 216 may be operatively coupled (e.g., via a wired or wireless connection) to one or more input devices 230 (e.g., a mouse, a keyboard, a touch-pad, a scroll-ball, a touch-display, a pen, a game controller, a voice input device, a scanning device, a digital camera, etc.) in such a fashion that input can be received from a user.

The communication connection(s) 1240 may enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Figure 6:
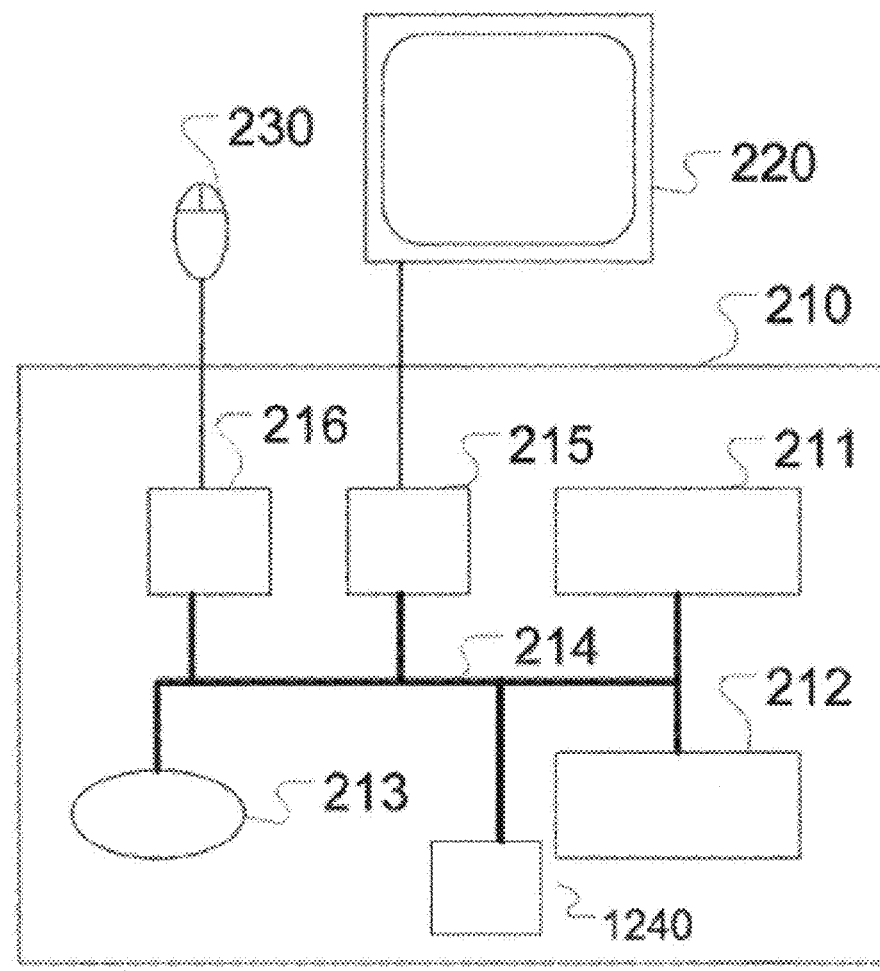
FIG. 6 is a schematic diagram of a computing system of one embodiment of the present disclosure.

FIG. 6 illustrates the computing device 210, the output device 220, and the input device 230 as separate devices for ease of identification only. However, the computing device 210, the output device(s) 220, and/or the input device(s) 230 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). The computing device 210 may be one or more servers, for example a farm of networked servers, a clustered server environment, or a cloud service running on remote computing devices.

The following exemplary embodiments further describe optional aspects of the presently disclosed technology and are part of this Detailed Description. These exemplary embodiments are set forth in a format substantially akin to claims (each set including a numerical designation followed by a letter (e.g., "A," "B," etc.), although they are not technically claims of the present application. The following exemplary embodiments refer to each other in dependent relationships as "embodiments" instead of "claims."

1A. A method comprising:
executing an ultrasound delivery plan in a checkerboard pattern.

2A. The method of embodiment 1A, wherein the plan includes energizing a transducer of a HIFU probe to deliver a thermal or cavitation dose of energy to ablate a designated treatment volume of a patient in the checkboard pattern.

3A. The method of embodiment 2A, wherein the power generated when energizing the transducer is higher than when ablating the entire designated treatment volume.

4A. The method of embodiment 1A, wherein predetermined areas of the designated treatment volume are skipped from applying or directly receiving ultrasound energy.

1B. A system or device configured to perform the method described and shown herein.

2B. The system or device of embodiment 1B, wherein total acoustic power is adjusted without negatively impacting energy deposition in a pre-focal zone while still achieving a contiguous volume ablation.

1C. A device configured to deliver a checkerboard pattern of ablation to create a plurality of spaced-apart lesions in or on a designated treatment volume.

2C. The device of embodiment 1C, wherein a level of energy used to create each lesion is higher than a level of energy used to ablate an entire designated treatment volume.

1D. A system for treating a targeted area of tissue with HIFU, the system comprising:

a probe including a transducer configured to emit ultrasound energy to deliver HIFU energy to a focal zone located within the targeted area; and a controller configured to supply and cease power to the transducer to deliver HIFU energy from the transducer and to cease delivery of HIFU energy from the transducer, the controller being configured to perform the following steps in series:

energize the transducer for a first predetermined amount of time to deliver a thermal or cavitation dose of energy to ablate a first lesion on or in the designated treatment volume at a first location;

de-energize the transducer for a second predetermined amount of time;

focus or move the transducer to a second location on or in the designated treatment volume, the second location being spaced-apart from the first location;

reenergize the transducer for the first predetermined amount of time to ablate a second lesion on or in the treatment volume;

de-energize the transducer for the second predetermined amount of time;

focus or move the transducer to a third location on or in the designated treatment volume, the third location being spaced-apart from each of the first and second location;

reenergize the transducer for the first predetermined amount of time to ablate a third lesion on or in the treatment volume; and de-energize the transducer for the second predetermined amount of time.

1E. A system for delivering high intensity focused ultrasound (HIFU) in a checkerboard pattern to a patient, the system comprising:

a HIFU probe assembly including at least one transducer configured to deliver ultrasound energy to a designated treatment volume located beneath subcutaneous fat of the patient;

one or more processors; and one or more memories operatively coupled to the one or more processors and having computer readable instructions stored thereon which, when executed by at least one of the one or more processors, causes the at least one of the one or more processors to selectively energize and de-energize the transducer to create a checkerboard pattern of lesions in the designated treatment volume.

2E. The system of embodiment 1E, wherein the transducer is energized to an increased power level to create each lesion.

3E. The system of embodiment 1E or 2E, wherein the increased power level is at least 26.4 W to compensate for skipping treatment sites.

4E. The system of embodiment 1E or 2E, wherein the increased power level is at least 31 W to compensate for skipping treatment sites.

5E. The system of embodiment 1E or 2E, wherein the increased power level is at least 40.7 W to compensate for skipping treatment sites.

6E. The system of embodiment 1E or 2E, wherein the increased power level is at least 49 W to compensate for skipping treatment sites.

While the presently disclosed technology has been described in detail and with reference to specific examples thereof, it will be apparent to one skilled in the art that various changes and modifications can be made therein without departing from the spirit and scope thereof. It is understood, therefore, that the presently disclosed technology is not limited to the particular embodiments disclosed, but it is intended to cover modifications within the spirit and scope of the presently disclosed technology as defined by the appended claims.

We claim:

1. A method comprising:

receiving a two-dimensional or three-dimensional image or rendering of a designated treatment volume of a patient, the designated treatment volume being a macroscopic three-dimensional volume located beneath subcutaneous fat of the patient, the image or rendering including a grid having a plurality of spaced-apart nodes;

planning a high intensity focused ultrasound (HIFU) tissue ablation treatment comprising identification of individual treatment sites of a plurality of planned treatment sites on any plane of the image or rendering, the planned treatment being independent of any characteristics of tissue of the designated treatment volume, the planned treatment including that one of the plurality of planned treatment sites is created at every other adjacent node of the plurality of spaced-apart nodes on the grid to create a checkerboard pattern;

placing a HIFU probe proximate a first location of the designated treatment volume of the patient and energizing a transducer of the probe to deliver a thermal or cavitation dose of ultrasound energy to ablate a first treatment site on or in the designated treatment volume at the first location, the first treatment site having a predetermined volume and being placed at one of the plurality of spaced-apart nodes of the grid;

de-energizing the transducer;

focusing or moving the transducer to a second location on or in the designated treatment volume, the second location being spaced-apart from the first location by at least a width of the predetermined volume such that any nodes of the plurality of spaced-apart nodes immediately adjacent to the first location are skipped or not ablated by the transducer;

reenergizing the transducer to deliver a thermal or cavitation dose of ultrasound energy to ablate a second treatment site on or in the treatment volume at the second location, the second treatment site having a size of the predetermined volume;

de-energizing the transducer for a second time;

focusing or moving the transducer to a third location on or in the designated treatment volume, the third location being spaced-apart from each of the first and second locations, the third location being spaced-apart from the second location by at least the width such that any nodes of the plurality of spaced-apart nodes immediately adjacent to the second location are skipped or not ablated by the transducer;

reenergizing the transducer to deliver a thermal or cavitation dose of ultrasound energy to ablate a third treatment site on or in the treatment volume at the third location, the third treatment site having a size of the predetermined volume; and de-energizing the transducer for a third time, wherein one of the plurality of spaced-apart treatment sites is created at every other adjacent spot on the grid to create the planned checkerboard pattern, and wherein the plurality of spaced-apart treatment sites coalesce into a single volumetric lesion to treat benign prostatic hyperplasia (BPH) or prostate cancer (PCa) of the patient.

2. The method of claim 1, wherein each step of de-energizing the transducer allows intervening tissue not part of the first, second, or third treatment site to cool to help manage build-up of thermal doses outside of a focal zone of the transducer.

3. The method of claim 1, wherein each step of energizing the transducer includes energizing the transducer for at least three seconds.

4. The method of claim 1, wherein the predetermined ablated tissue volume is between $3\times3\times10$ mm$^3$ and $3\times3\times12$ mm$^3$.

5. The method of claim 1, wherein the first, second, and third treatment sites form part of a plurality of spaced-apart treatment sites, the plurality of spaced-apart treatment sites being four or more spaced-apart treatment sites.

6. A method comprising:

placing a probe proximate a first location of a designated treatment volume of a patient and energizing a transducer of the probe to ablate a first treatment site on or in the designated treatment volume;

de-energizing the transducer;

focusing or moving the transducer to a second location on or in the designated treatment volume, the second location being spaced-apart from the first location;

reenergizing the transducer to ablate a second treatment site on or in the treatment volume;

de-energizing the transducer for a second time;

focusing or moving the transducer to a third location on or in the designated treatment volume, the third location being spaced-apart from each of the first and second location;

reenergizing the transducer to ablate a third treatment site on or in the treatment volume; and de-energizing the transducer for a third time, wherein each treatment site is located at one of every other adjacent node on a grid of a three-dimensional image or rendering of the designated treatment volume of the patient to create a checkerboard pattern, wherein the plurality of spaced-apart treatment sites coalesce into a single volumetric lesion to treat benign prostatic hyperplasia (BPH) or prostate cancer (PCa) of the patient.

7. The method of claim 6, prior to each of the above steps the method further comprising:

receiving the three-dimensional image or rendering of the designated treatment volume of the patient, the image or rendering including the grid; and planning a high intensity focused ultrasound (HIFU) tissue ablation treatment comprising identification of individual treatment sites on any of three planes of the three-dimensional rendering, wherein each treatment site corresponds to one of the nodes of the grid, the planned treatment being independent of any characteristics of tissue of the designated treatment volume.

8. The method of claim 7, wherein the designated treatment volume is a macroscopic three-dimensional volume located beneath subcutaneous fat of the patient, and wherein each step of de-energizing the transducer allows intervening tissue not part of the first, second, or third treatment site to cool to help manage build-up of thermal doses outside of a focal zone of the transducer.

9. The method of claim 8, wherein a discontinuous tissue ablation pattern is maintained in both a sagittal plane and a transversal plane.

10. The method of claim 6, wherein the steps of energizing or reenergizing the transducer include reaching an acoustic power level to compensate for skipping treatment sites.

11. A system for delivering high intensity focused ultrasound (HIFU) in a checkerboard pattern to a patient, the system comprising:

a HIFU probe assembly including at least one transducer configured to deliver ultrasound energy to a designated treatment volume located beneath subcutaneous fat of the patient;

one or more processors; and one or more memories operatively coupled to the one or more processors and having computer readable instructions stored thereon which, when executed by at least one of the one or more processors, causes the at least one of the one or more processors to perform the following in series:

a) energize the transducer for a first predetermined amount of time to deliver a thermal or cavitation dose of ultrasound energy to ablate a first treatment site on or in the designated treatment volume at a first location, the first location being positioned on one node of a grid of a two-dimensional or three-dimensional image or rendering of the designated treatment volume of the patient;

b) de-energize the transducer for a second predetermined amount of time;

c) focus or move the transducer to a second location on or in the designated treatment volume, the second location being spaced-apart from the first location such that any nodes of the grid immediately adjacent to the first location are skipped or not ablated by the transducer;

d) reenergize the transducer for the first predetermined amount of time to ablate a second treatment site on or in the treatment volume at the second location;

e) de-energize the transducer for the second predetermined amount of time;

f) focus or move the transducer to a third location on or in the designated treatment volume, the third location being spaced-apart from each of the first and second location such that nodes of the grid immediately adjacent to the second location are skipped or not ablated by the transducer;

g) reenergize the transducer for the first predetermined amount of time to ablate a third treatment site on or in the treatment volume at the third location; and h) de-energize the transducer for the second predetermined amount of time;

i) wherein the plurality of spaced-apart treatment sites coalesce into a single volumetric lesion to treat benign prostatic hyperplasia (BPH) or prostate cancer (PCa) of the patient.

12. The system of claim 11, wherein each treatment site has a predetermined volume between $3\times3\times10$ mm$^3$ and $3\times3\times12$ mm$^3$, wherein the first treatment site is separated from the second treatment site by at least 3 mm, wherein the second treatment site is separated from the third treatment site by at least 3 mm.

* * * * *